(12) United States Patent
Guglielmino et al.

(10) Patent No.: US 11,982,679 B2
(45) Date of Patent: May 14, 2024

(54) CONFORMATIONAL MIMOTOPES FOR DETECTING SPECIFIC ANTIBODIES

(71) Applicant: DISTRETTO TECNOLOGICO SICILIA MICRO E NANO SISTEMI S.C.A.R.L., Catania (IT)

(72) Inventors: Salvatore Guglielmino, Catania (IT); Laura Maria De Plano, Catania (IT); Santina Carnazza, Catania (IT); Domenico Franco, Catania (IT); Alessandra Nicoletti, Catania (IT); Mario Zappia, Catania (IT); Sabrina Conoci, Catania (IT); Salvatore Petralia, Catania (IT)

(73) Assignee: DISTRETTO TECNOLOGICO SICLILIA MICRO E NANO SISTEMI S.C.A.R.L., Catania (IT)

( * ) Notice: Subject to any disclaimer, the term of this patent is extended or adjusted under 35 U.S.C. 154(b) by 1212 days.

(21) Appl. No.: 16/464,197

(22) PCT Filed: Nov. 27, 2017

(86) PCT No.: PCT/IB2017/057422
§ 371 (c)(1),
(2) Date: May 24, 2019

(87) PCT Pub. No.: WO2018/096512
PCT Pub. Date: May 31, 2018

(65) Prior Publication Data
US 2019/0383834 A1    Dec. 19, 2019

(30) Foreign Application Priority Data

Nov. 28, 2016  (IT) .......................... 102016000120204

(51) Int. Cl.
| G01N 33/68 | (2006.01) |
| C07K 7/08 | (2006.01) |
| C12N 15/10 | (2006.01) |
| G16B 15/00 | (2019.01) |
| G16B 45/00 | (2019.01) |

(52) U.S. Cl.
CPC .......... G01N 33/6896 (2013.01); C07K 7/08 (2013.01); C12N 15/1037 (2013.01); G16B 15/00 (2019.02); G16B 45/00 (2019.02); *G01N 2333/4709* (2013.01); *G01N 2800/2821* (2013.01)

(58) Field of Classification Search
None
See application file for complete search history.

*Primary Examiner* — Aurora M Fontainhas
(74) *Attorney, Agent, or Firm* — Thomas | Horstemeyer, LLP (57) ABSTRACT

The present invention relates to a method for obtaining protein mimotopes occurring in at least two distinct 3D conformations. In a further embodiment, a method for detecting antibodies with diagnostic relevance using said mimotopes is claimed. In a preferred embodiment, said methods are applied to Alzheimer's disease.

3 Claims, 7 Drawing Sheets

Specification includes a Sequence Listing.

*CLONE 12III1*

CLUSTAL X (1.83/2.1) multiple sequence alignment Identity Matrix

```
ab1-42       -DAEFRHDSGYEVHHQKLVFFAEDVGSNKGAIIGLMVGGVVIA
12III1-pVIII AEGEFRWPPHFEWHFD-------DGDPAKAAFDSLQASATE--
             :.***   . :* *.:       *  .. *.*: .*  ....
             1              15      23                39
```

B

*CLONE 12cIII1*

CLUSTAL X (1.83/2.1) multiple sequence alignment Identity Matrix

```
ab1-42       DAEFRHDSGYEVHHQKLVFFAEDVGSNKGAIIGLMVGGVVIA-------------
12cIII1-pVIII -AEG---------------EFGG---GCIEGPCLEGPDPAKAAFDSLQASATE
              **                 *  *   *.* *  ;  *    *
              2 3              16 22                   38  42
```

C

*CLONE 12CIII4*

CLUSTAL X 2.1 multiple sequence alignment Identity Matrix

```
ab1-42       -DAEFRHDSGYEVHHQ▓▓▓▓▓DVGS-NKGAIIGLMVGGVVIA--
12cIII4-pVIII --AEG------EFHRGCIEGPCLDAPDPAKAAFDSLQASATE----
              **          *.*:  :   . *.. . *.*: .*  ....
              2 3         11                        34  39
```

CONFORMATIONAL MIMOTOPES FOR DETECTING SPECIFIC ANTIBODIES

CROSS-REFERENCE TO RELATED APPLICATIONS

This application is the 35 U.S.C. § 371 national stage application of PCT application No. PCT/IB2017/057422, filed Nov. 27, 2017, where the PCT claims the priority to and benefit of Italian Patent Application No. 102016000120204, filed Nov. 28, 2016 both of which are herein incorporated by reference in their entireties.

SEQUENCE LISTING

This application contains a sequence listing filed in ST.25 format entitled "221007-1660 Sequence Listing" created on Jan. 25, 2023. The content of the sequence listing is incorporated herein in its entirety.

FIELD OF INVENTION

The present invention relates to a method for obtaining protein mimotopes occurring in at least two distinct 3D conformations. In a further embodiment, a method for detecting antibodies with diagnostic relevance using said mimotopes is claimed. In a preferred embodiment, said methods are applied to Alzheimer's disease.

BACKGROUND ART

According to the estimates reported by the World Alzheimer Report in 2015, there are 46.8 million people in the world living with a form of dementia. The most common of these forms, with an incidence between 50 and 70% of all forms of dementia, is Alzheimer's disease (AD). AD evolves until compromising, in an affected patient, the ability to perform daily actions.

The analysis and monitoring of two proteins, amyloid P protein 1-42 (Aβ42) and Tau protein, are to date fundamental instruments for a correct and early diagnostic classification of AD. However, these analyses require diagnostic techniques of the invasive type. Alternative approaches have been developed, with uncertain results.

The detection of AD-specific biomarkers present in the serum is the approach of choice. It is known that autoantibodies against Aβ42 are naturally present in human blood, in free or antigen-complexed form, both in AD patients and in healthy subjects (Szabo et al 2008, Gustaw et al 2008). The levels thereof change with the progression of the disease, but the data reported in the literature relating to antibody values present in the serum are conflicting. A series of works describe decreased serum levels of free β-autoantibodies, not attached to the antigen, decreased in AD patients with respect to the controls (Song et al 2007, Moir et al 2005, Weksler et al 2002, Du et al 2001, Britschgi et al 2009, Brettschneider et al 2005); on the other hand, another series of works reports increased values (Nath et al 2003, Mruthinti et al 2004), or unchanged values (Hyman et al 2001, Baril et al 2004). The studies mentioned above are mainly focused on autoantibodies against Aβ42 monomer.

Therefore, it is assumed that autoantibodies against the oligomer or aggregated Aβ42 were the most clinically relevant target (Hock et al 2003). Titration methods of autoantibodies in serum have been proposed by acid dissociation of β-immune complexes, highlighting higher Aβ-specific antibody levels in patients affected by AD with respect to healthy controls (Gustaw et al 2008, Gustaw-Rothenberg et al 2010). However, using a similar procedure, Klaver et al (2011) have not found any significant difference between the two groups, AD and control.

The data inhomogeneity obtained to date does not make a diagnostic approach based on the evaluation of the autoantibodies against the Aβ42 protein feasible.

A non-invasive and accurate diagnostic method is strongly felt, which allows the diagnosis of AD, as well as of other pathologies characterized by the presence of proteins taking on more than one 3D conformation, even in early stages of the pathology. A method is equally strongly felt, which allows, having identified the protein responsible for the disease and the 3D conformations which it takes on, to efficiently develop antibodies capable of recognizing it.

It is the object of the present invention to identify methods and instruments for developing diagnostic and/or therapeutic methods with the desired features.

SUMMARY OF INVENTION

The variability of the data found in the vast literature available about autoantibody levels against Aβ42 has led to assuming that different and distinct Aβ42 variants or multimers, involved in AD, may be recognized as conformational antigens. This could lead to the generation of different antibody populations, not equally recognizable with the different approaches followed in the different studies. The presence of different autoantibodies would, therefore, be considered responsible for the variability of the observed data.

The authors of the present invention surprisingly developed a completely new approach allowing the identification of mimotopes conformationally homologous to Aβ42. Said mimotopes, or sequences capable of mimicking conformational epitopes of a protein, have been successfully used as a probe for identifying specific AD antibodies in diagnostic systems.

The approach herein described for the first time has an application thereof for identifying mimotopes of any protein which is in more than one conformation. The patent may be extended to all the pathologies caused by the alteration of proteins which from the standard conformation generate misfoldings, thus becoming pathological. The altered protein forms could lead to the exposure of new epitopes, potentially involved in the antibody response. Included in these pathologies are: prion proteins involved in Creutzfeldt-Jakob disease; synuclein which, transformed into α-synuclein, leads to the formation of fibrillar forms in Parkinson's disease; huntingtin, involved in Huntington's disease; phosphorylated Tau, involved in neurodegenerative diseases; amyloidosis, characterized by the deposition at the extracellular level of protein material with a β-sheet structure, which is the reason why the use of the term β-fibrillosis is preferred for the disease, β-fibrillosis involving different proteins, including 2β-microglobulin, transthyretin, lysozyme, fibrinogen; poly(A)-binding proteins, involved in oculopharyngeal muscular dystrophy; proteins of the Serpin superfamily (serine protease inhibitor). Therefore, the present invention relates to a method for obtaining mimotopes for proteins of interest. By way of example, said method is successfully applied for obtaining mimotopes of proteins selected from the group comprising: Aβ42, antibodies responsible for autoimmune diseases, prion proteins, synuclein, huntingtin, phosphorylated Tau, 2β-microglobulin, transthyretin, lysozyme, fibrinogen, poly(A)-binding proteins, proteins of the Serpin superfamily (serine protease inhibitor).

The present invention further relates to a diagnostic method comprising the use of phage clones expressing protein mimotopes of diagnostic relevance for the evaluation of the presence of specific antibodies for said protein in the serum.

The present invention also relates to the use of a target against which to generate antibodies capable of recognizing and binding proteins of therapeutic interest. In a preferred embodiment, said protein of therapeutic interest is Aβ42 and said target is the Chaperon protein caf1M of *Yersinia pestis*.

Phage clones are also described which comprise the sequences SEQ ID No. 1, SEQ ID No. 4, SEQ ID No. 5 and the use thereof in AD diagnosis and in generating therapeutic antibodies capable of recognizing and binding Aβ42.

Also claimed are the sequences SEQ ID No. 1, SEQ ID No. 4, SEQ ID No. 5 and the use thereof in AD diagnosis and/or in generating therapeutic antibodies capable of recognizing and binding Aβ42. In a preferred embodiment, said peptide sequences are synthesis sequences.

DESCRIPTION OF THE DRAWINGS

FIG. 1: 3D representation of the 10 conformational prediction models obtained for the single Aβ42.

FIG. 2: 3D representation of the 10 conformational prediction models obtained for the fibrillar Aβ42.

FIG. 3: 3D structure of the single Aβ42 conformational homology—Chaperon protein caf1M. A) 3D structure that highlights the conformational homology region in the AA between the position 20-36 of Aβ42 in single form with the AA 149-161 of the Chaperon protein caf1M. B) AA sequence of the two proteins having the same conformation.

FIG. 4: A) 3D structure highlighting the conformational homology region in the AA between the position 1-10 of fibrillar Aβ42 with the AA 20-29 of the Chaperon protein caf1M. B) AA sequence of the two proteins having the same conformation.

FIG. 5: 3D structure highlighting the conformational homology region between Aβ42 in single form (in gray) and Chaperon protein caf1M (in black).

FIG. 6: 3D structure highlighting the conformational homology region between fibrillar Aβ42 (in gray) and Chaperon protein caf1M (in black).

FIG. 7: alignment of the clone sequences 12III1 (A, SEQ ID NO:1), 12cIII1 (B, SEQ ID NO:4) and 12cIII4 (C, SEQ ID NO:5) along the portions of conformational interest on the caf1M (SEQ ID NO:7 or 8) and with Aβ42 (SEQ ID NO:6).

FIG. 8: alignment of the insert and of the amino acids exposed along the pVIII clone sequences 12III1 (A, SEQ ID NO:10), 12cIII1 (B, SEQ ID NO:11) and 12cIII4 (C, SEQ ID NO:12) with Aβ42 (SEQ ID NO:9).

FIG. 9: reactivity of the phage clone 12III1 against the sera of AD patients and sera of control subjects (CTR).

FIG. 10: electrochemical cell with 3 electrodes.

The present invention relates to a method for obtaining mimotopes of proteins of interest characterized by occurring in at least two distinct 3D conformations, wherein said method comprises:

a) Obtaining, by means of bioinformatics tools known and available to those skilled in the art, the at least two 3D conformations of the test protein;
b) Performing, by means of bioinformatics tools known and available to those skilled in the art, conformational homology analyses for the two or more conformations obtained in step a), and selecting from protein databases the protein(s) having the greatest homology with the conformations of the test protein; by way of example, said databases are available through Ncbi;
c) Optionally, confirming the homology querying the 3D structure of the one or more proteins selected in step b) and analyzing the returned proteins, among which the test protein must also be present;
d) Identifying, in silico, the conformational homology region between the test protein and the protein(s) selected as homologous;
e) Selecting an antibody recognizing said conformational homology region, referred to as a bait antibody;
f) Providing the serum of at least one subject, in which serum an antibody capable of recognizing the test protein is expressed;
g) Providing a phage library;
h) Selecting and amplifying, in said phage library, clones reactive against said bait antibody and against said serum of at least one subject, wherein the sequence expressed by said clones is the mimotope of the test protein.

In a preferred embodiment, said procedure of selecting the phage library comprises three selection cycles. In the first cycle, the phage population capable of binding the IgG-test protein is isolated. The eluted phages in the first step are used in the second selection cycle for screening against the monoclonal bait. Only the phages which cross react with the IgG-test protein and with the bait antibody have the possibility of being selected. Lastly, a third selection cycle is carried out, directed again against the test IgG-protein, so as to select the phage clones having more affinity for the latter.

Preferably, said test IgG-protein and said bait antibody are immobilized on beads, for example on Dynabeads Protein G. Typically, the selected phage clones are amplified and the DNA thereof sequenced. From the obtained genomic sequences, encoded amino acid sequences are thus deduced, by means of bioinformatics programs, for example using ExPASy.

Phage clones expressing protein mimotopes with diagnostic relevance are applied in diagnostic methods, wherein said method comprises:

a) Providing at least one phage clone expressing at least one mimotope of a protein with therapeutic relevance;
b) Incubating, with methods known to those skilled in the art, said at least one phage clone with a test serum;
c) Reading, with methods known in the prior art, the accomplished reaction between said phage clone and antibodies possibly contained in said serum.

Typically, an ELISA assay is used and the reading carried out is of the colorimetric type. The accomplished reaction is indicative of the presence of the researched antibody with diagnostic relevance in the test serum.

In a further embodiment, it is herein claimed the use of selected mimotopes as described above for generating antibodies capable of recognizing and binding proteins of therapeutic interest. By way of a non-limiting example, said protein of therapeutic interest is Aβ42 and said target is the Chaperon protein caf1M of Yersinia pestis. As an alternative, said method provides the use not of the entire protein but of the fragment thereof for which the greatest conformational homology with the protein of interest has been shown. Said fragment has a diagnostic or therapeutic value, as described above, where said protein fragments are used for generating antibodies which recognize and bind proteins of interest.

In a particularly preferred embodiment, the ELISA assays are performed on chips, wherein the selected phage clone is immobilized on a chip then exposed to the serum of interest. Typically, said chips allow a reading of the optical, electrochemical or capacitive type.

The following examples aim at describing particularly preferred embodiments of the invention, not to be understood as limiting the scope of the present invention.

Example 1: Obtaining 3D Conformation Models of Single and Fibrillar Aβ42

Through the use of bioinformatics platforms, proteins have been researched which optionally had conformations homologous to Aβ42. Through the use of the bioinformatics tool UniProt the sequence of the APP (Amyloid Precursor Protein, UniProt ID:P05067) protein was studied which is a transmembrane macroprotein of 770 amino acids (aa) with the extracellular N-terminus (amino-terminus) and the cytoplasmic C-terminus (carboxyl-terminus), encoded by a gene located on chromosome 21. The APP is known to be cleaved in a series of functional fragments by proteases, the secretases.

Figure 1:
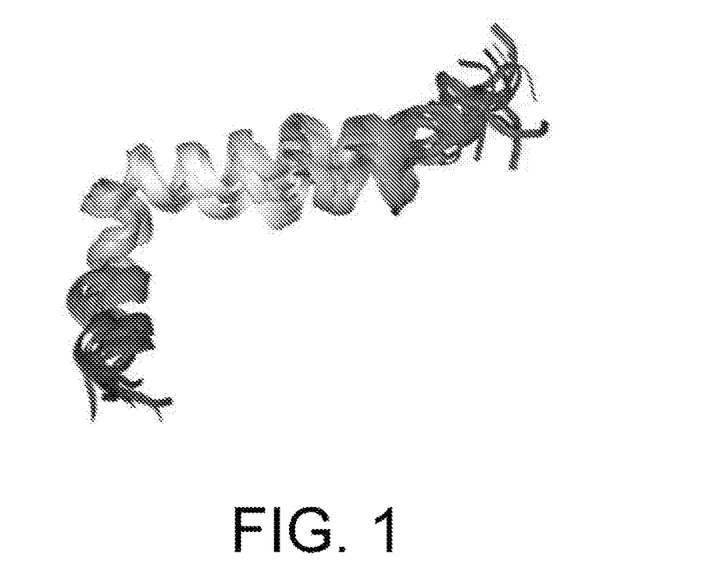
Figure 2:
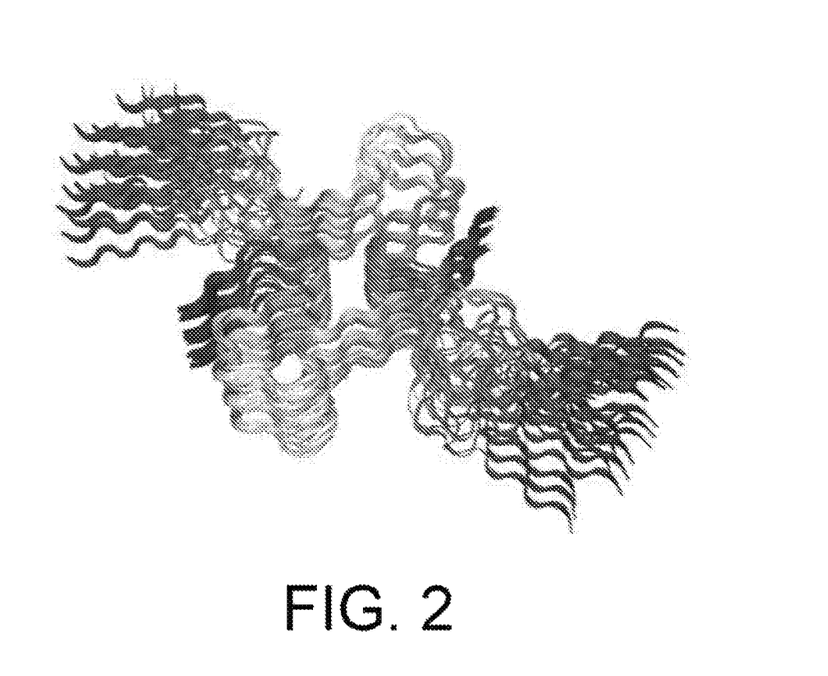
Figure 3:
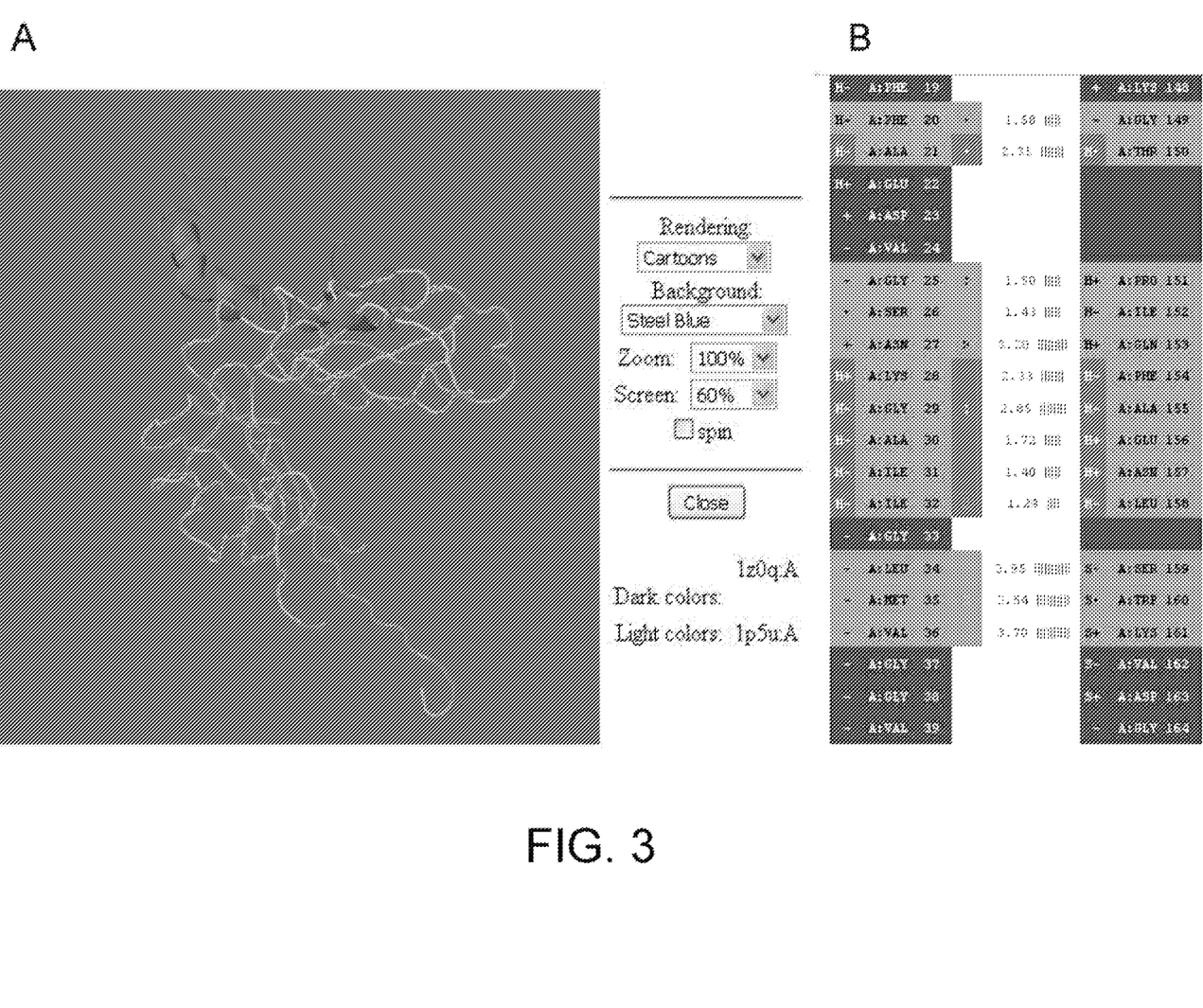
Figure 4:
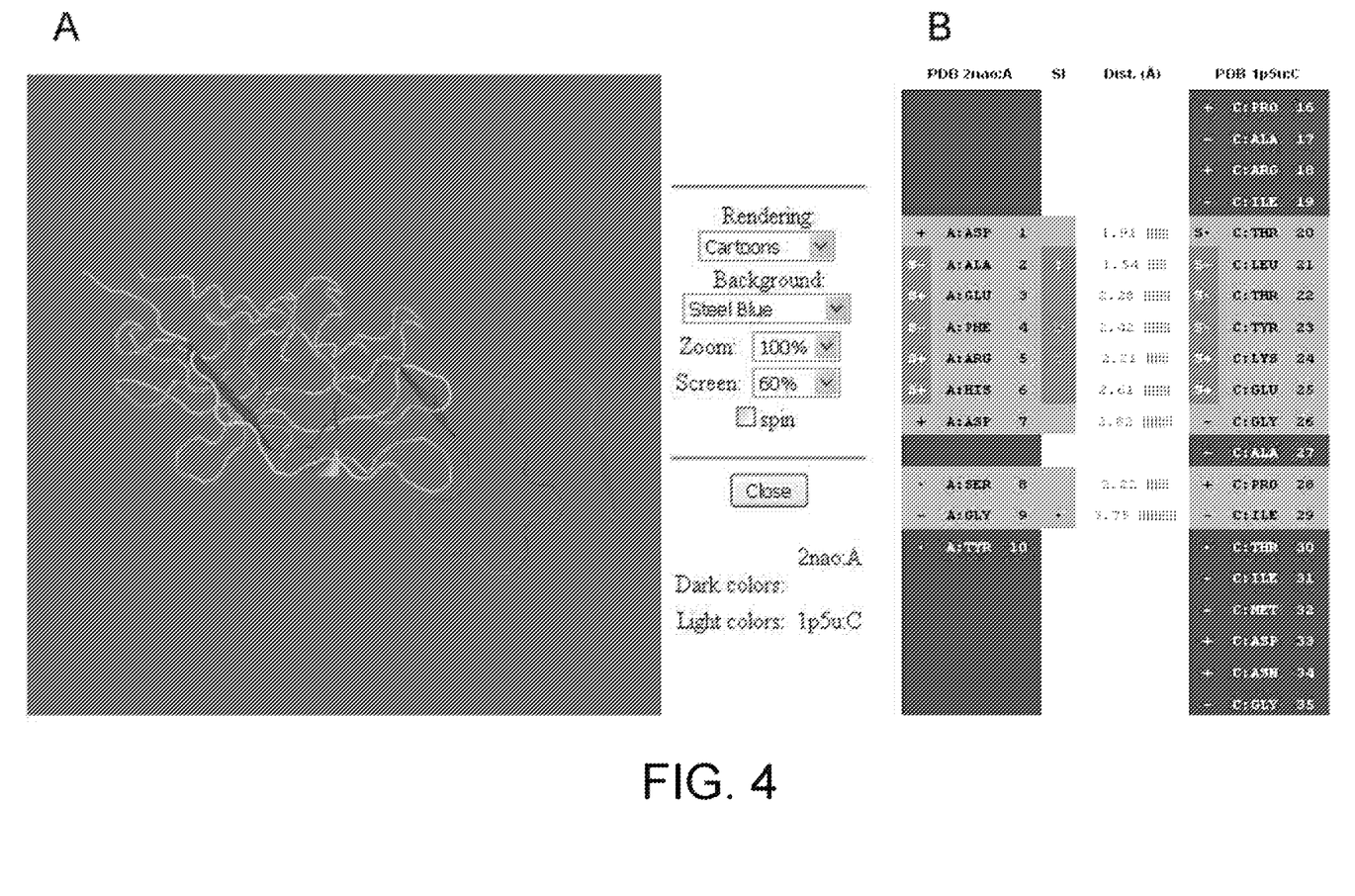
Figure 5:
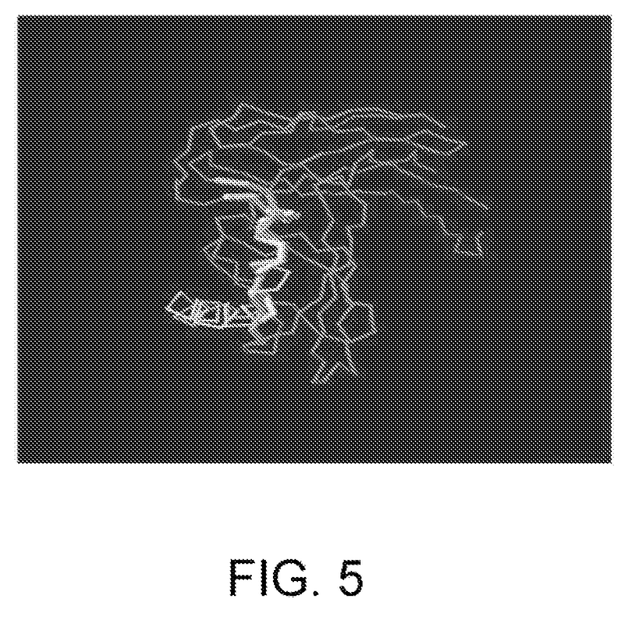
Figure 6:
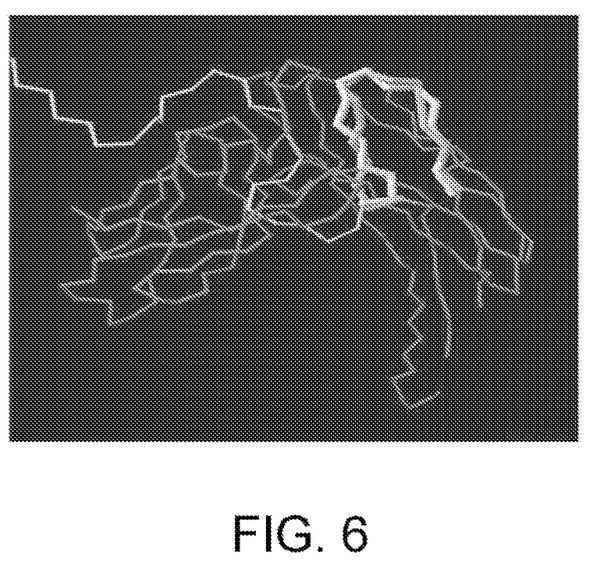

The mechanism which leads to the formation of Aβ42 by APP provides a β-secretase (BACE: beta APP cleavage enzyme) intervention which cleaves on the extracellular domain, at amino acids 671-672. With the instruments Protein Data Bank (PDB) and 3D Molecular Viewer, the 3D conformations of Aβ42 in the different conformations thereof, single and fibrillar, have been identified and reprocessed. The returned structures are 10 possible conformation models which the single considered protein may assume in the aqueous medium and 10 possible conformation models for the same fibrillar protein. In FIG. 1 the 3D structures of Aβ42 in single form are shown. In FIG. 2 the 3D structures of Aβ42 in fibrillar form are shown.

Having the models obtained as described above, conformational homology analyses were conducted, using the bioinformatics instrument PDBeFold (EMBL-EBI). The analysis carried out is based on identifying residues occupying an equivalent geometric shape in space. The bioinformatics platform allowed a comparison between the 3D structures in the FDB database with the "bait" sequence selected by us (query sequence). The conformation alignment between the 3D structures of Aβ42 in the different conformations thereof was performed by setting, one at a time, all the filters proposed by the system, that is: Q-score (Cα-alignment); P-score (which takes into consideration RMSD, the number of aligned residues, any gaps, the number corresponding to secondary structure elements); Z-score (which takes into account the Gaussiane statistics); % of sequence identity.

With this approach, the system returned a series of proteins. Those having only one homology section either for single Aβ42 or for fibrillar Aβ42 were discarded, and on the other hand those proteins having a homology for both forms were selected. A protein being homologous to more Aβ42 conformations was thus identified, the Chaperon protein caf1M (PDB ID=1p5u) of *Yersinia pestis*. To confirm the conformational homology, the same approach followed using the 3D structure of Aβ42 in PDB as bait was carried out, using the 3D structure of the Chaperon protein caf1M as bait. The returned proteins as homology output were analyzed and Aβ42 resulted therefrom.

FIGS. 3, 4, 5 and 6 show the 3D structures of the conformational homology of the proteins in question. From FIG. 3, it is noted that Aβ42 in single form has a conformational homology in the amino acids (aa) comprised between the position 20 and 36, with the aa arranged on the Chaperon protein caf1M between the position 149 and 161. The portion highlighted with the darker color in the image refers to the conformational homology region between the two proteins. To the side, it is noted the aa sequence of the two proteins having the same conformation.

FIG. 4 shows Aβ42 in fibrillar form having a conformational homology in the aa between the position 1-10 with the aa arranged on the Chaperon protein caf1M from the position 20-29. The portion highlighted with the darker color in the image is the conformational homology region between the two proteins. To the side it is shown the aa sequence of the two proteins having the same conformation.

The conformational homology was also verified with another bioinformatics instrument in PDB, instrument allowing to identify a conformational homology on the secondary structure between the proteins of interest. In this bioinformatics platform, the homology with Chaperon protein Caf1M of the different Aβ42 forms is present in the points highlighted in FIGS. 5 and 6.

In FIG. 5, the single Aβ42 and the Chaperon caf1M is shown. The homology is present on the single Aβ42 in the region 1-20, on the Chaperon protein caf1M in the region 148-168 with a p-value=9.75 e-01.

With Aβ42 in fibrillar form, FIG. 6, the homology is present in the regions 27-42 and on the Chaperon protein caf1M, in the region 18-33 aa with a p-value=9.14 e-01.

The conformational homology found between the different forms taken by Aβ42 and the Chaperon protein caf1M confirms the non-probability that these are randomly similar. In fact the homology found in multiple elements of the same working matrix, in different points of a same protein increases the probability that these are actually shared, and which therefore the homology thereof is no coincidence (Bastas G et al. 2008). Having found a sufficient degree of conformational homology between Aβ42 in single form and Aβ42 in fibrillar form on the Chaperon protein caf1M implies that the latter protein includes more misfolding forms, or more conformations, of the Aβ42 protein.

Example 2: Selecting Phage Libraries

Having identified the protein(s) with a high degree of conformational homology, specifically the Chaperon protein caf1M, monoclonal antibodies were used directed against the same for selecting, by cross selections against IgG in sera of patients affected by AD, different phage libraries constructed on the pVIII of the filamentous bacteriophage M13, through the Phage Display technique.

For the screening of any conformational mimotopes, homologous to caf1M of *Yersinia pestis*, the monoclonal antibody YPF19 (AbDSerotec® A Bio-Rad Company) anti-F1 of Y. pestis was used, reactive only against the EV76 Y. pestis strain, as it recognizes discontinuous epitopes on the Chaperon protein caf1M. Furthermore, the antibody used is capable of recognizing different Yersinia pestis fragments equal and/or homologous to the Chaperon protein caf1M region comprised between the aa of positions 1-160, region which is that of interest for the conformational homology with the different forms of Aβ42.

As a source of antibodies directed against possible conformational epitope of human Aβ42, a pool of 5 human sera from AD patients (IgG-AD) (average age of 77.4 years, average MMSE value=15.2) was selected to be used.

Material preparation protocol for the selection: Phage libraries. Phage M13 libraries were used, kindly donated by Prof. Franco Felici, expressing random peptides, exposed on the pVIII protein, based on the phagemid vector pC89 (Felici et al., 1991) on which random oligonucleotide sequences were inserted in the region 5' of the VIII gene present in the vector, under the control of the LacZ promoter. The digestion with the restriction enzymes EcoRI and BamHI linearized the vector and allowed the insertion of the oligonucleotides with random sequences which, flanked by the same restriction sites, allow the recircularization of the vector through ligase reaction.

For the selection, two types of peptide libraries were used, expressing twelve amino acids in the pVIII amino terminus region: pVIII-12aa and pVIII-12aa-cys, wherein the latter has a cysteine-cysteine constriction expressed in the peptide, so as to stabilize the structure thereof. The amplitude of the library is comprised between 10 and 100 million independent clones.

Monoclonal antibody YPF19 anti-F1 of *Yersinia pestis*: AbDSerotec® A Bio-Rad Company IgG1-9820-5007.

Human AD antibodies: pool of 5 human sera from AD patients (average age of 77.4 years, average MMSE value=15.2) (IgG-AD). For the immobilization of the antibodies, Dynabeads® Protein G (Thermo Fischer scientific) super magnetic beads of 2.8 μm were used. The saline solutions used to form the reaction buffers were purchased at Sigma Aldrich.

Coating Procedure:

Coating of the Dynabeads® Protein G with the monoclonal antibody YPF19:

1) Take 50 μl of Dynabeads® Protein G and resuspend them in 500 μl of citrate-phosphate buffer pH 5 in Eppendorf tubes; put under stirring at 8 rpm for 10'.
2) Separate with a magnetic device for 1-2', then aspirate and eliminate the supernatant. Repeat twice steps 1 and 2.
3) Add 100 μl of mAbs anti-F1 *Yersinia pestis*, where the stock solution is diluted 1:48 so as to have 20.8 μl of antibody diluted in 979.2 μl of PBS/Tween 20 0.5% and a final concentration of 5 mg in 100 μl.
4) Incubate for 60' at room temperature (RT) under mild stirring in inclined rotation (8 rpm).
5) Separate the Dynabeads, now functionalized with the mAb anti-F1 *Yersinia pestis* (DYN-mAbYPF19) with a magnetic device for 2' and eliminate the supernatant.
6) Wash the DYN-mAbYPF19 twice with 200 μl Conjugation Buffer (20 mM sodium phosphate, 0.15 M NaCl, pH 7-9). Separate the Dynabeads, functionalized with the mAb anti-F1 *Yersinia pestis* (DYN-mAbYPF19) with a magnetic device for 2' and eliminate the supernatant.
7) Wash the DYN-mAbYPF19 twice with 200 μl Conjugation Buffer (20 mM sodium phosphate, 0.15 M NaCl, pH 7-9).
8) Resuspend the Dynabeads in 250 μl of 5 mM BS3 ((bis(sulfosuccinimidyl)suberate).
9) Incubate at room temperature for 30' with inclination/rotation.
10) Block the crosslinking reaction by adding 12.5 μL of Quenching Buffer, from 25 mM to 60 mM Tris.
11) Incubate at room temperature for 15' with inclination/rotation.
12) Wash the Dynabeads three times with 200 μl PBST (or IP Buffer of choice). Position the magnet and discard the supernatant.
13) Resuspend the DYN-mAbYPF19 in 1 ml of storage solution, that is PBS+1% BSA+0.01% Tween 20 pH 7.4. Coat the Dynabeads® Protein G with the AD sera pool.

The procedure for coating the Dynabeads® Protein G described above was carried out except for step 3), changed as follows:

3) Add 100 μl of AD sera pool containing diluted IgG-AD 1:10.

Library Pretreatment

100 μl of each library ($1 \times 10^{12}$ viral particles) were added to 50 μl of Dynabeads® Protein G and resuspended in 190 μl of TBS-Tween 0.1%. After 30' incubation, separation with a magnetic device for 1-2'; the supernatant is recovered and used to carry out again the two preceding steps twice before the use of the library for the selection.

New Selection Procedure Methodology

Example 3: Isolating Phages of Interest, "Double Binding" Procedure

In order to isolate phages expressing common sequences recognized both by the monoclonal YPF19 and by the human sera pool IgG-AD, a selection procedure referred to as "double-blinding" was developed.

In brief, 3 selection cycles were carried out for each library, referred to as biopanning cycles, using the same execution protocol. This cross-selection procedure allows, in the first round, to select the phage population capable of binding the IgG-AD immobilized on the beads. The eluted phages in this step are used in the second selection round, for screening against the monoclonal YFP19. In this case, only the phages which cross react also with the monoclonal YPF19 will have the possibility of binding the target, so as to limit the number of reactive phages to those common between the two antibody classes IgG-AD and mAb-YPF19. Another biopanning cycle is then carried out, with the eluted phages from the second selection round, again against the IgG-AD, in order to select the phage pools having more affinity for the latter.

First Selection Round 1) 100 μL of each of the two phage libraries 12aa and 12aa-cys with a titer of $10^{12}$ are added to 500 μl of Dynabeads IgG-AD and placed to incubate for 3 h at RT under mild stirring.
2) Separation with a magnetic device for 1-2' and elimination of supernatants containing the phages which did not bind the target present on the functionalized beads.
3) Elution of the selected clones with 500 μl of eluting buffer, 0.2 M of glycine-HCl (pH 2.2)+0.1% BSA.
4) Immediate neutralization of the phage eluate with 100 μl of Tris-HCl buffer 1 M, pH 9.1.
5) Amplification of the eluted transfecting units, precipitation and titration according to the respective protocols, described hereinafter, for use in the subsequent round.

Second Selection Round
1) 100 μL of phage precipitate of the first selection round are added to 500 μl of Dynabeads-mAbYPF19 and placed to incubate for 3 h at RT under mild stirring.
2) Separation with a magnetic device for 1-2' and elimination of supernatants containing the phages which did not bind the target present on the functionalized beads.
3) Elution of the selected clones with 500 μl of eluting buffer 0.2 M of glycine-HCl (pH 2.2)+0.1% BSA.
4) Immediate neutralization of the phage eluate with 100 μl of Tris-HCl buffer 1 M, pH 9.1.
5) Amplification of the eluted transfecting units, precipitation and titration according to the respective protocols, described hereinafter, for use in the subsequent round.

Third Selection Round
1) 100 μl of phage precipitate of the second selection round are added to 500 μl of Dynabeads IgG-AD and placed to incubate for 3 h at RT under mild stirring.
2) Separation with a magnetic device for 1-2' and elimination of supernatants containing the phages which did not bind the target present on the functionalized beads.
3) Elution of the selected clones with 500 μl of eluting buffer 0.2 M of glycine-HCl (pH 2.2)+0.1% BSA.
4) Immediate neutralization of the phage eluate with 100 μl of Tris-HCl buffer 1 M, pH 9.1.
5) Amplification of the eluted transfecting units, precipitation and titration according to the respective protocol, and use for the subsequent analyses.

Example 4: Amplifying Selected Phages

Materials: IPTG stock (11.9 mg/ml) Molecular Biology Certified; Ampicillina stock solution (100 mg/ml) Sigma Aldrich; Kanamycin stock solution (10 mg/ml) Sigma Aldrich; X-Gal stock Molecular Biology Certified.

The saline solutions used to prepare the buffers and all the reagents used for the procedure were purchased at Sigma Aldrich. TBS (50 mM Tris-HCl pH 7.5, 150 mM NaCl); PEG 20% NaCl 2.5 M. Amplification of the eluates coming from the first, second and third selection rounds:

I Step (Plate Amplification)
1) Incubate an *E. coli* TG1 colony at 37° C. in LBphage under stirring up to OD600=0.8.
2) Infect 800 μl of this culture with 200 μl of eluted phage suspension coming from selection.
3) The sample is incubated at 37° C. without stirring for 15', then for 20' under stirring.
4) Inoculate the entire aliquot, equal to 1 ml of infected cell suspension, on LA+Glucose, +Amp in 120 mm plates and incubate at 37° C. for 12-16 h.
5) Pour, on the obtained cells mat, 8 ml of LBphage with 5 μl ampicillin (Stock sol. 100 mg/ml) and 2 ml of glycerol (final concentration 20%).
6) Recover the cells with a spatula and transfer them into 20 ml tubes.
7) Store at −20° C. (scraping).

II Step (Liquid Amplification)
1) Incubate 50 μl of infected cells coming from the scraping in 10 ml of LB+Amp 5 μl (of the stock solution 100 mg/ml) and incubate at 37° C. under stirring until reaching an OD600=0.2.
2) Add to the culture 10 μl of helper phage M13KO7 (Stock sol. $10^{12}$ phage/ml) and 20 μl of IPTG (Stock sol. 11.9 mg/ml) in order to have a final concentration of 109 phage/ml.
3) Incubate the sample at 37° C. without stirring for 15', then for 4 h under stirring.
4) Centrifuge at 3000 rpm (1090×g, Beckman rotor JA-20108) for 40' at 4° C.; recover the supernatant to which sodium azide (4 μl of the stock solution 5% per recovered ml) is added. Store at 4° C. (amplification of the selected phage eluate).

Precipitation of the amplified product coming from the eluate of the three selection rounds:
1) Add 800 μl of 20% PEG/NaCl 2.5 M to 3.2 ml of amplified phage supernatant. Let decant at 4° C. for 12-16 h.
2) Centrifuge at 1200 rpm (with Eppendorf refrigerated benchtop centrifuge 5417R, 15300×g) for 30' at 4° C.
3) Eliminate the supernatant and the pellet is resuspended in 320 μl of TBS1×.
4) Add 80 μl of PEG/NaCl 2.5 M 20% and incubate the sample in ice for 1 h.
5) Centrifuge at 12000 rpm for 30' at 4° C.;
6) The supernatant is discarded and the pellet is resuspended in 32 μl of TBS 1×;
7) Incubate at 70° C. for 15', in order to eliminate any *E. coli* cells.
8) Store at 4° C.

Titration Procedure

The titration is carried out to determine the number of infecting phage particles per μl. Two different phage titration protocols were carried out.

First Protocol
1) Incubate an *E. coli* TG1 colony at 37° C. in LBphage under stirring up to OD600 of 0.8.
2) Collect 10 μl of precipitate and add it to 90 μl of TBS (dilution 10-1); carry out decimal dilutions with the same volumes up to the dilution 10-9.
3) Infect 90 μl of *E. coli* TG1 with 10 μl of the phage dilutions comprised between 10-5 and 10-9.
4) Incubate the test samples at 37° C., leaving them in stasis for 15' and then under stirring for 20'.
5) Pour 90 mm plates and incubate for 12-16 h at 37° C.
6) From the number of *E. coli* colonies grown on the medium and considering the dilution factor, the number of TU/ml can be derived.

According to the protocol, physical titration by a UV/Vis spectrophotometer reading.
1) Place 1 ml of phage precipitate in a quartz microcuvette.
2) Place the cuvette in the dedicated compartment of the spectrophotometer; carry out the reading at a wavelength of 269 nm.
3) Through the obtained absorbance value, it will be possible to derive the concentration in TU/ml as the value OD=1 corresponds to $2.2 \times 10^{12}$ PFU/ml (Li et al. 2010).

Table 1 shows the values obtained from the different selection rounds, indicating the input of the quantity of engineered bacteriophages placed at the start of the bioplanning process (IN), the quantity recovered at the end of the process (OUT), and finally the ratio between them (YIELD) to indicate the number of bacteriophages that have instead remained adhered to the selection target:

TABLE 1

| | Cross-selection IgG-AD/IgG-YPF19 12aacys-cys | | | Cross-selection IgG-AD/IgG-YPF19 12aa | | |
|---|---|---|---|---|---|---|
| | IN | OUT | yield | IN | OUT | yield |
| I sel (IgG-AD) | $3.5 \times 10^{12}$ | $3.3 \times 10^{7}$ | $9.43 \times 10^{-6}$ | $1.5 \times 10^{12}$ | $1.3 \times 10^{7}$ | $8.67 \times 10^{-6}$ |
| II sel (IgG-YPF19) | $1.45 \times 10^{13}$ | $4.2 \times 10^{9}$ | $2.9 \times 10^{-4}$ | $1.7 \times 10^{13}$ | $2.65 \times 10^{9}$ | $1.56 \times 10^{-4}$ |
| III sel (IgG-AD) | $3.6 \times 10^{12}$ | $3.65 \times 10^{6}$ | $1.01 \times 10^{-4}$ | $5.32 \times 10^{12}$ | $8.25 \times 10^{8}$ | $1.55 \times 10^{-4}$ |

Selection of positive clones for both antibodies of interest
The phage clones coming from the third round were used in a double immunoscreening assay which allows to identify, in a phage population, the positive clones against the antibodies of interest.

1) Incubate an *E. coli* TG1 colony at 37° C. in LBphage under stirring up to OD600 of 0.6.
2) Collect 10 µl of precipitate and add it to 90 µl of TBS (dilution 10-1); carry out the decimal dilutions with the same volumes up to the dilution 10-5.
3) Infect 90 µl of *E. coli* TG1 with 10 µl of the phage dilutions comprised between 10-3 and 10-5.
4) Incubate the test samples at 37° C., leaving them in stasis for 15' and then under stirring for 20'.
5) Pour the solution entirely on LA+Amp+Kan+IPTG in 90 mm plates and incubate for 12-16 h at 37° C.
6) For the dilution plates in which there is a number of colonies comprised between 50 and 100, the protocol is carried out. 7) Place nitrocellulose filters (Trans-Blot Transfer Medium 0.45 mm Bio-RAD) on the plate.
8) Add the buffer for replica-plating and lightly press to make it adhere to the medium.
9) Close the plate and leave at RT for 1 h. Two filters in a sequence were prepared for each test.
10) Transfer the filter in a new sterile petri plate with the colonies facing upwards; then, coat with 10 ml of Blocking buffer 1× (PBS+milk 5%+Tween 20 0.5%).
11) Leave to incubate for 1 h and 30' under pivoting stirring (velocity 45-50 rpm) at RT.
12) Eliminate the Blocking buffer and wash the filters immersing in ultra pure sterile H₂O for 1'.

To check the reactivity against the monoclonal YPF19:
1) coat the filter with 6 ml of monoclonal antibody YPF19 diluted 1:100 in PBS+1% milk+0.1% Tween 20.
2) incubate 2 h under pivoting stirring (velocity 45-50 rpm) at RT.
3) wash the filter 3 times with 10 ml of Washing Buffer (PBS+Tween 20 0.05%), 5' for each wash, on the pivoting stirrer (velocity 45-50 rpm) at RT.
4) Eliminate the Washing Buffer and add 6 ml of anti-mouse-HRP (Abcam ab97023) diluted 1:50,000 in PBS+milk 1%+Tween 20 0.01%. 5) wash the filter 3 times with 10 ml of Washing Buffer as in 2).
6) Add 6 ml of Stable DAB Invitrogen and leave from 3' to 15' at RT under stirring.
7) Eliminate the DAB, the filter is left to dry.

Check reactivity against the AD sera pool:
1) coat the filter with 6 ml of AD sera pool in PBS+1% milk+0.1% Tween 20.
2) Incubate 2 h under pivoting stirring (velocity 45-50 rpm) at RT.
3) wash the filter 3 times with 10 ml of Washing Buffer, 5' for each wash, on the pivoting stirrer (velocity 45-50 rpm) at RT.
4) Eliminate the Washing Buffer and add 6 ml of anti-human-HRP (IgG Fc AP113P) diluted 1:15,000 in PBS+milk 1%+Tween 20 0.01%.
5) wash the filter 3 times with 10 ml of Washing Buffer as in 2).
6) Add 6 ml of Stable DAB Invitrogen and leave from 3' to 15' at RT under stirring.
7) Eliminate the DAB, the filter is left to dry.

The colonies, which were reactive in both filters, were individually amplified.

Example 5: Amplification and Precipitation of the Single Reactive Clones

1) Incubate an *E. coli* TG1 colony infected by the reactive clone from the immunoscreening in 10 ml of LB phage+5 µl of Ampicillina (stock solution 100 mg/ml) at 37° C. under stirring up to a OD600 of 0.2.
2) Add 20 µl of IPTG (Stock sol. 11.9 mg/ml) and 20 µl helper M13K07 titer 1×10¹² PFU/ml (to have a final concentration of ~109 phages/ml),
3) Incubate at 37° C. for 30' in stasis and 30' under stirring at 220 rpm;
4) transfer the culture into 250 ml of LB phage+125 µl of Ampicillin (stock solution 100 mg/ml) and incubate at 37° C. under stirring overnight at 220 rpm.
5) Collect the culture in two 250 ml sterile test tubes (Nalgene type) and centrifuge at room temperature for 30' at 9820×g.
6) Recover the supernatant and transfer it into two new 250 ml sterile test tubes;
7) Repeat the centrifugation as described above;
8) Filter the entire amplification in the filtering apparatus with a dedicated 0.45 µm filter at low protein avidity (in PVDF) to remove the bacterial cell residues,
9) Add sodium azide (4 µl of the stock solution 5% per ml of phage suspension) and store at 4° C.

The amplified of single clones are precipitated as follows:
1) Aliquot the filtrate in 2 250 ml sterile test tubes with 125 ml each;
2) Add in each ¼ of the volume of PEG/NaCl (that is 31.25 ml); Incubate in an ice bath for 1 h and 30';
3) Centrifuge at 4° C. at 15300×g. Discard the supernatant and resuspending each pellet in 12.5 ml of TBS; combine the suspensions in a single test tube (total volume 25 ml);
4) Add ¼ of the volume of PEG/NaCl (that is 6.25 ml) and incubate in an ice bath for 1 h and 30';
5) Centrifuge at 4° C. for 45' at 15300×g; Discard the supernatant and resuspend the pellet in 5 ml of TBS;
6) titrate according to the protocol described above and store at 4° C. (labelling as precipitate of the respective phage clone). 14 positive clones were obtained from the immunoscreening of the library of 12aa, two of these resulted significantly reactive for both assayed sera; 22 reactive clones were obtained from the library 12cys-cys, of which 4 resulted a greater reactivity for both assayed sera.

Example 6: Confirm Binding Specificity, ELISA Assay

An ELISA assay was carried out adsorbing the selected single clones on ELISA well plates (Multisorp Nunc) to confirm the binding specificity with the monoclonal antibody YPF19 and with the IgG-AD of the AD sera pool used for the selection.
1) Place 100 µl at the concentration of $10^{12}$ of phage precipitate of the desired clones into of 96 well plates (Multisorp, Nunc, Roskilde, Denmark) For each sample the experiment was conducted in triplicate.
2) Leave to adhere to the bottom, incubating ON at 4° C.
3) After incubation, eliminate the supernatant and add 300 µl of Blocking Buffer (PBS-Tween 20 0.05%-Non Fat Dry Milk 6%) in each well; incubate for 2 h at 37° C. in stasis.
4) Eliminate the Blocking Buffer washing once for 3' with 300 µl Washing buffer with the Immuno-Wash 12 Nunc.

Check the monoclonal antibody YPF19 specificity:
1) 100 µl of mAb (anti F1 YPF19 diluted 1:100 in PBS-Tween 20 0.1%+Non Fat Dry Milk 1%) are added. The samples are left to incubate for 2 h at 37° C. under stirring.
2) Eliminate the supernatant and wash 3 times with Washing buffer as described above.
3) Discard the Washing buffer, in each well add 100 μl of conjugated anti-mouse-HPR antibody (Abcam ab97023), diluted 1:50,000 in PBS-Tween 20 0.1%+ Non Fat Dry Milk 1% and incubate for 1 h at 37° C. under stirring
4) Wash with Washing buffer 5 times as described above.
5) Add 100 μl of TMB, incubate the plate in the dark at room temperature for 30'-45'.
6) Block the reaction with 100 μl of 1N HCl.
7) Carry out the reading with ELISA reader (Labsystem Multiskan Bichromatic) at the wavelength of 450 nm.

To check the specificity of response with the AD sera pool:

1) 200 μl of AD sera pool are added to the dilution 1:10 in PBS Tween 20 0.1%+Non Fat Dry Milk 1%. The samples are left to incubate for 1 h at 37° C. under stirring.
2) Eliminate the supernatant and wash 10 times with Washing buffer as described above.
3) Discard the Washing buffer, and add 100 μl anti-human-HPR antibody (IgG Fc AP113P), diluted 1:15,000 in PBS-Tween 20 0.1%+Non Fat Dry Milk 1%. Leave to incubate for 1 h at 37° C. under stirring.
4) Wash with Washing buffer 5 times as described above.
5) Then, proceed with the addition of 100 μl of TMB, incubate the plate in the dark at room temperature for 30'-45'.
6) Block the reaction with 100 μl of 1N HCl.
7) Carry out the reading with ELISA reader (Labsystem Multiskan Bichromatic) at the wavelength of 450 nm. The PBS was used as a negative control for the evaluation of the non-specific binding background.

Example 7: Sequencing of the Selected Clones

The selected clones which simultaneously show greater reactivity against the two antibody categories, or IgG present in the serum of AD subjects and specific monoclonal antibodies for the identified proteins having a high conformational homology degree for Aβ42, were sequenced and therefore the compatibility with the predicted 3D conformational homology regions was evaluated.

From the analyzed clones, the clone referred to as 12III1 was selected, capable of discriminating a pool of IgG-AD through the ELISA test.

The DNA thereof was amplified for PCR, sequenced and the amino acid sequences encoded from the same were deducted from the obtained genome sequences.

The clone 12III1 expresses the sequence RWPPHFEWHFDD (SEQ ID No.1). The testing was extended against samples of AD patient sera and of controls, showing the capability of discriminating between the two assayed population types, with significance greater than 99% (pValue=0.0044). Furthermore, through the ELISA test with Urea, a high binding avidity was observed by the clone 12III1 against the antibodies IgG-AD.

For the amplification of the DNA, protocols known to those skilled in the art were carried out, herein summarized:

1) Incubate an *E. coli* TG1 colony at 37° C. in LBphage under stirring up to O.D.600 of 0.8.
2) Infect 80 μl of this culture with 20 μl of suspension of the phage clone of interest.
3) Incubate at 37° C. without stirring for 15', then for 20' under stirring.
4) Carry out an isolation in LA+Amp in 90 mm plates and incubate at 37° C. for 12-16 h;
5) Collect an *E. coli* TG1 colony infected by the clone and dilute it in 20 μl H2O.
6) Place 1 μl of solution containing the sample in the reaction mix used for the PCR consisting of: 21.25 μl of sterile $H_2O$ PCR, 10 μl of Buffer, 5 μl of each primer E24, SEQ ID No. 2 5'GCTACCCTCGTTCCGATGCTGTC 3', −40 RE, SEQ ID No. 3 5'GTTTTCCCAGTCACGAC 3'.
7) The mix was then denatured in a thermal cycler for 10' at 95° C., and then 0.25 μl of my TAQ were added. Each sample was subjected to the following PCR cycles: [4' at 94° C.; 25 cycles of: 30" 94° C./30" 52° C./30" 72° C.; 7' 72° C.].
8) At the end of the process 35 μl were used for DNA purification, the balance of the sample was displayed after 30' of electrophoresis run in a 2% agarose gel with 2.5 μl of ethidium bromide.

For the subsequent sequencing, the DNA was purified with the extraction kit Nucleo Spin® (Macherey-Nagel).

Besides the already mentioned clone 12III1, the following further reactive clones were also identified:

12-cyc-cys, referred to as 12cIII1, sequence GGGCIEGPCLEG (SEQ ID No. 4).

12-cyc-cys, referred to as 12cIII4, sequence HRGCIEGPCLDA (SEQ ID No. 5).

The clones showing a greater reactivity were analyzed in the amino sequences thereof. The peptides were then compared for sequence and frequency homology of the single amino acids, among those of the same group.

Through the CLUSTAL X sequence alignment program, using the BLOSUM matrix (Thompson, J. D., D. G. Higgins, and T. J. Gibson. 1994. NucleicAcids Res. 22:4673-4680), the clone sequences were aligned along the portions of interest conformational on the chaperon protein caf1M (that is the fragments 20-29 and 148-161) and with the Aβ42; the results are shown in FIG. 7.

The clones isolated from the two libraries have a low homology degree both with the portion of the Caf1 involved in the recognition and with the Aβ42, as expected since they are not linear epitopes. With the CLUSTAL X program, tracts which are homologous to the two Aβ42 regions, as well as to the chaperon protein caf1M fragments, were identified.

Figure 7:
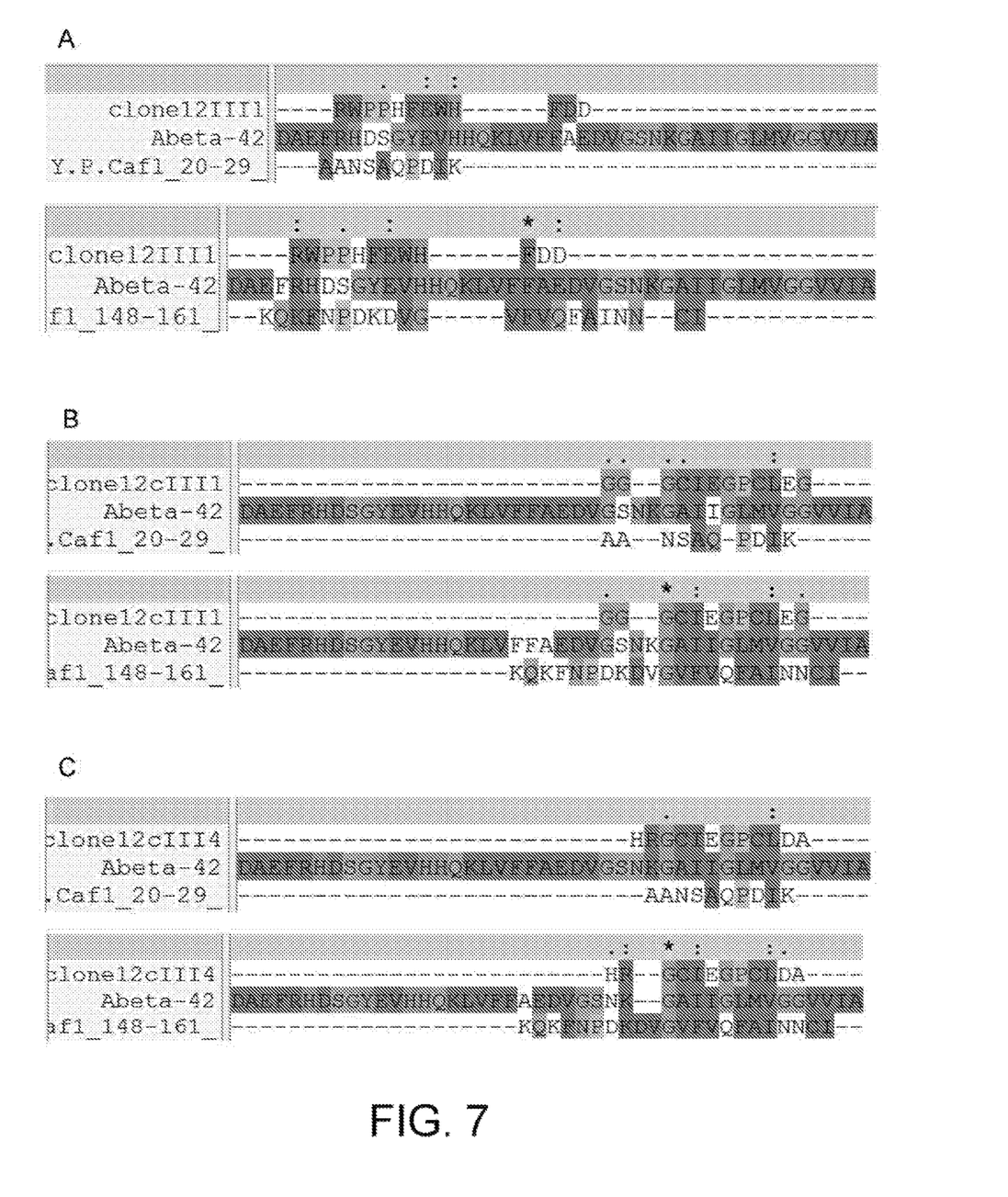

The clone 12III1, coming from the library 12-mer, has a homology along the initial region of the Aβ42, FIG. 7, panel A, unlike the clone sequences 12cIII1 and 12cIII4, isolated from the selection conducted on the libraries 12-mer (cys-cys), which instead have a homology with the end part of the Aβ42, FIG. 7, panels B and C.

Figure 8:
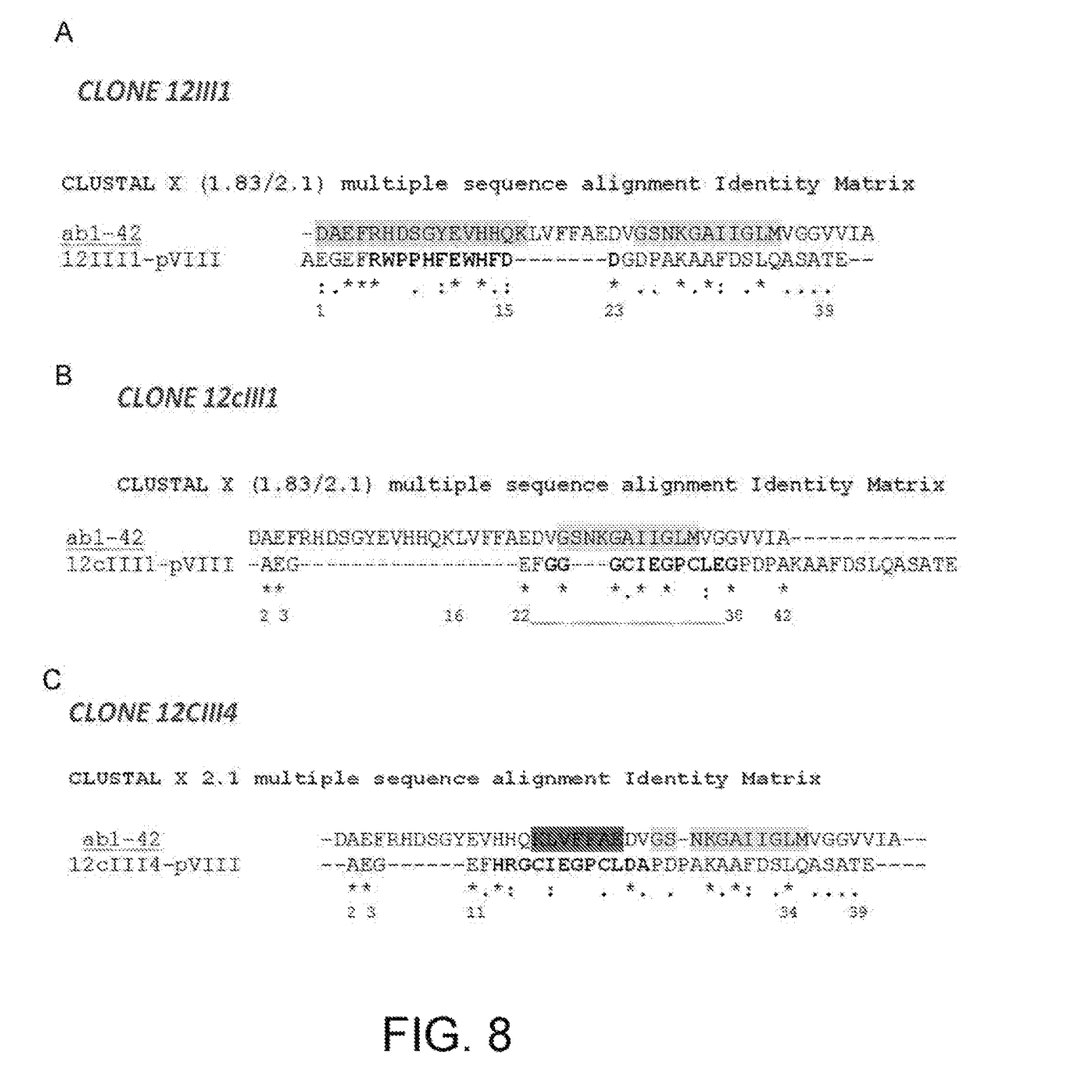

Furthermore, the alignment was carried out on the Aβ42 of the clone sequences which have besides the insert also the amino acids that are exposed along the pVIII, which may give a contribution to the recognition participating to the correct folding of the peptide. The results are shown in FIG. 8.

The clone 12III1 (panel A) aligns on the region (1-16) of the Aβ42, region implicated in the recognizing by the immunoglobulins and in the formation of amyloid protofilaments. The clone 12cIII1 (panel B) aligns along the region (25-35), known as the shortest Aβ42 fragment which exhibits the beta-sheet structure (Hughes et al 2000). The clone 12cIII4 (panel C) aligns with the region (16-22) which represents the hydrophobic core of the Aβ42 mainly subject to aggregation, known as the autorecognition site (Neddemiep et al 2011).

It is possible to note how also in the presence of the remaining part of pVIII, the peptide maintains, in any case, the same homology region with the Aβ42, if not for some position changes of a few amino acids. Only the clone 12cIII4 is more affected by the presence of amino acids along the pVIII.

Example 8: Diagnostic Test for AD

The three phage clones selected in the above-described examples were simultaneously tested against a sera pool of 5 healthy subjects, (MMSE>26, no pathology of the nervous system), homogeneous in age, average age=77.2 years and with the AD sera pool used for the screening, average age=77.4 years. Therefore an ELISA test was developed, adsorbing on the bottom of the wells logarithmic scale dilutions of the phage clone 12III1 ($10^{10}$, $10^{11}$, $10^{12}$, $10^{13}$ PFU/ml) and concentrations of sera equal to 1:10, 1:50 and 1:100. The procedure was standardized using the phage concentration at $1 \times 10^{12}$ PFU/ml (OD269~1), and the serum dilution at 1:50. Below is the description of the optimized procedure of the test.
1) Place 100 µl of desired clones into the concentration of $10^{12}$ of precipitated phage in 96 well plates (Multisorp, Nunc, Roskilde, Denmark). For each sample, the tests were conducted in triplicate.
2) Leave to adhere to the bottom, incubating ON at 4° C.
3) After incubation, eliminate the supernatant and add 300 µl of Blocking Buffer (PBS-Tween 20 0.05%-Non Fat Dry Milk 6%) in each well and incubate for 2 h at 37° C. in stasis.
4) Eliminate the Blocking Buffer and wash the single wells once (for 3') with 300 µl Washing buffer (PBS-Tween 20 0.05%) with the Immuno-Wash12 Nunc.
5) Add 200 µl of AD sera pool, or of control sera pool to the dilution 1:10 in PBS-Tween 20 0.1%+Non Fat Dry Milk 1%. The samples are left to incubate for 2 h at 37° C. under stirring. 6) Eliminate the supernatant and wash 10 times with Washing buffer as described above.
7) Discard the Washing buffer, and adding 100 µl of conjugated anti-human IgG HPR antibody (IgG Fc AP113P), diluted 1:15,000 in PBS-Tween 20 0.1%+Non Fat Dry Milk 1%. Leave to incubate 1 h at 37° C. under stirring.
8) Wash with Washing buffer 5 times as described above.
9) Add 100 µl of TMB, incubate the plate in the dark at room temperature for 30'-45'.
10) Block the reaction with 100 µl of 1N HCl.
11) Carry out the reading with ELISA reader (Labsystem Multiskan Bichromatic) at the wavelength of 450 nm. The PBS was used as a negative control for the evaluation of the non-specific binding background.

The values obtained by the test are shown in table 2, wherein the average value of the obtained results from the three repetitions of each sample was inserted; the significance was evaluated with the Student test.

TABLE 2

| Clones | Patient pool AD | Subject pool Control | t-test |
|---|---|---|---|
| 12III1 | 1.266 | 0.464 | Pvalue = 0.03 (significance at 95%) |
| 12cIII1 | 0.55 | 0.33 | Not significant |
| 12cIII4 | 0.64 | 0.31 | Not significant |

The obtained results show that only the clone 12III1 discriminates with significance the two subject groups. Therefore the preferred embodiment of the present invention is the phage clone 12III1 and the use thereof as an antigenic mimotope to determine the antibody levels IgG-AD.

In order to validate the system, 20 patients affected with AD with a MMSE index comprised between 20.8-6.8 and 18 healthy controls were recruited and the samples were tested according to the ELISA method as follows:
1) Place 100 µl at the concentration of $10^{12}$ of phage precipitate of the desired clones into a 96 well plate (Multisorp, Nunc, Roskilde, Denmark). For each sample the tests were conducted in triplicate.
2) Leave to adhere to the bottom, incubate ON at 4° C.
3) After incubation, eliminate the supernatant and add 300 µl of Blocking Buffer (PBS-Tween 20 0.05%-Non Fat Dry Milk 6%) in each well and incubate for 2 h at 37° C. in stasis.
4) Wash the single wells once (for 3') with 300 µl Washing buffer (PBS-Tween 20 0.05%) with the Immuno-Wash12 Nunc.
5) Add 200 µl of respective sample sera to the dilution 1:10 in PBS-Tween 20 0.1%+Non Fat Dry Milk 1%. The samples are left to incubate for 2 h at 37° C. under stirring.
6) Eliminate the supernatant and wash 10 times with Washing buffer as described above.
7) Discard the Washing buffer, and add 100 µl of anti-human IgG HPR antibody (IgG Fc AP113P) diluted 1:15,000 in PBS-Tween 20 0.1%+Non Fat Dry Milk 1%. Leave to incubate for 1 h at 37° C. under stirring.
8) Wash with Washing buffer 5 times as described above.
9) Add 100 µl of TMB, incubating the plate in the dark at room temperature for 30'-45'.
10) Block the reaction with 100 µl of 1N HCl.
11) Carry out the reading with ELISA reader (Labsystem Multiskan Bichromatic) at the wavelength of 450 nm.

The PBS was used as a negative control for the evaluation of the non-specific binding background.

Figure 9:
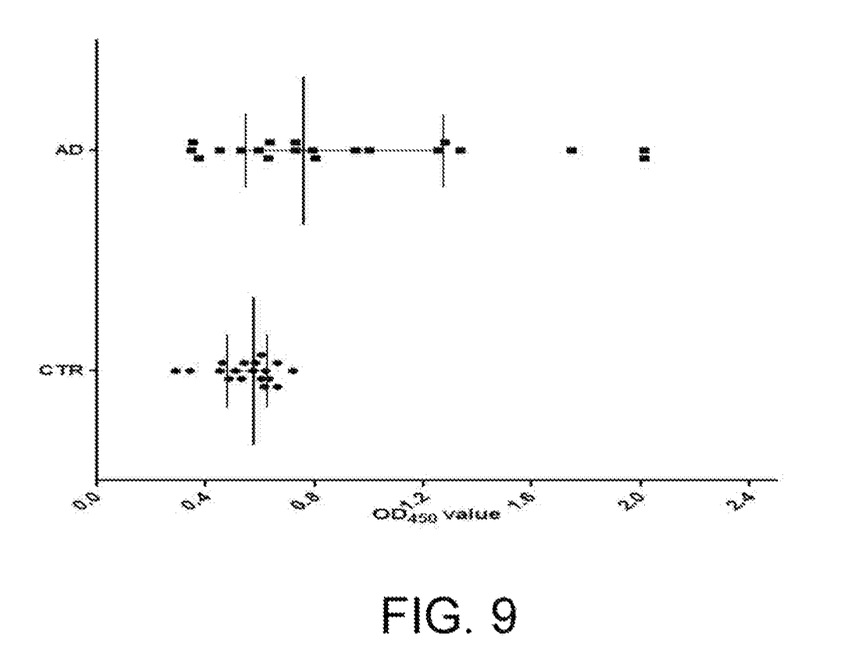

The obtained results are shown in FIG. 9.

The difference between the averages of the healthy control group and those relating to the AD patients, is significant at 99% (pValue=0.0044).

It was then tested whether the antibodies in the sera of the patients with AD which recognize the peptide sequence of 12III1 would show a low or high avidity, through the ELISA test with the use of the Urea 4M. The test was conducted on 20 samples, 10 AD sera and 10 control sera, according to the following protocol:

1) Place 100 µl at the concentration of $10^{12}$ of phage precipitate of the desired clones into 96 well plates (Multisorp, Nunc, Roskilde, Denmark) For each sample the tests were conducted in triplicate.
2) Leave to adhere to the bottom, incubate ON at 4° C.
3) After incubation, eliminate the supernatant and add 300 µl of Blocking Buffer (PBS-Tween 20 0.05%-Non Fat Dry Milk 6%) in each well and incubate for 2 h at 37° C. in stasis.
4) Wash the single wells once (for 3') with 300 µl Washing buffer (PBS-Tween 20 0.05%) with the Immuno-Wash12 Nunc.
5) Add 200 µl of respective sample sera to the dilution 1:10 in PBS-Tween 20 0.1%+Non Fat Dry Milk 1%. The samples are left to incubate for 2 h at 37° C. under stirring.
6) Eliminate the supernatant and wash 10 times with 250 µl of a Urea solution 4M-Tween 20 0.5% in PBS of about 3'.
7) Discard the Washing buffer and add 100 µl of anti-human IgG HPR antibody (IgG Fc AP113P) diluted 1:15,000 in PBS-Tween 20 0.1%+Non Fat Dry Milk 1%. Leave to incubate for 1 h at 37° C. under stirring.
8) Wash with Washing buffer 5 times as described above.
9) Add 100 µl of TMB, incubate the plate in the dark at room temperature for 30'-45'.
10) Block the reaction with 100 µl of 1N HCl.
11) Carry out the reading with ELISA reader (Labsystem Multiskan Bichromatic) at the wavelength of 450 nm. The PBS was used as a negative control for the evaluation of the non-specific binding background.

The avidity (Avi %) is evaluated determining the ratio between the obtained result without the use of Urea and that obtained after treatment with Urea.

The avidity test showed that the treatment with Urea does not significantly alter the bond with the target (average avidity % of the considered samples=81%, comprised between 121.53 and 61.33). For such a reason it is required that the antibodies bound by the phage clone 12III1 are free antibodies at a high avidity.

Example 9: Implementation on a Chip for Integrated Detection

Optical Detection

It was obtained using a device consisting of a silicon chip (substrate) and a polycarbonate plastic support which creates a reaction chamber of a volume of about 400 µl. In particular, said substrate has a dimension of about 1.2*1.7 cm and is coated with a layer of aluminum, typically with a thickness of 1 µm on which a layer of SiO2 (TEOS 8000 A) lies. With the aim of obtaining a stable bond between said support and the bacteriophage, a functionalization is carried out which provides the use of a coupling agent such as for example 1-Ethyl-3-(3-dymethylaminopropyl) carbodiimide (EDC).

The wells are coated with 20 µl of MES buffer (ethanesulfonic acid 2-(N-morpholine)) and left to decant in stasis for 10'.

From the moment of use, a solution of 10 mg EDC/250 µl of MES is prepared and the same is dispensed in each well wherein 10 µl of phage suspension of the clone 12III1 (measuring $1.4 \times 10^{13}$ PFU/ml) is then added, to have a total final concentration of $1 \times 10^{11}$ phages in the reaction.

The chip is incubated for 2 h at room temperature in a humid room in stasis. After eliminating the supernatant and washing the well with 20 µl of PBS for 5', the blocking solution (PBS+MILK 6%+Tween 20 0.05%) is added and the chip is incubated in a humid room for 2 h in stasis at room temperature. Finally, the supernatant is eliminated and a further wash is carried out as described above. An ELISA test is then carried out on the silicon surface, operating as follows:

dispensing, in the wells chips functionalized with the phage clone 12III1, 20 µl of AD serum or CTR diluted 1:50 in dilution buffer (PBS+1% MILK+Tween 20 0.05%) and incubating in a humid room at 37° C. for 1 hour under mild stirring (100 rpm)

eliminating the excess and carrying out 10 washes of 3' each with 20 µl of washing buffer (PBS+Tween 20 0.05%)

adding 20 µl of anti-human IgG HPR (IgG Fc AP113P) and incubating in the dark at 37° C. for 1 h under mild stirring (100 rpm)

eliminating the excess and carrying out 5 washes of 3' under stirring at 50 rpm adding 100 µl of TMB, incubating the plate in the dark at room temperature for 30'-45' blocking the reaction with 100 µl of 1N HCl carrying out the reading with ELISA reader (Labsystem Multiskan Bichromatic) at the wavelength of 450 nm. The PBS was used as a negative control for the evaluation of the non-specific binding background.

The conducted experiment had the following results (the numbers refer to the spectrophotometer reading):

AD serum 1: 0.939
AD serum 2: 0.787
CTR serum: 0.230

As an alternative to the optical detection, electrochemical detection may be used. In this case, a silicon chip is used on the surface of which electrodes to form an electrochemical cell were integrated, according to the diagram shown in FIG. 10. Typically, each electrochemical cell (1) comprises three electrodes: reference (2), working (4) and counter (3).

Figure 10:
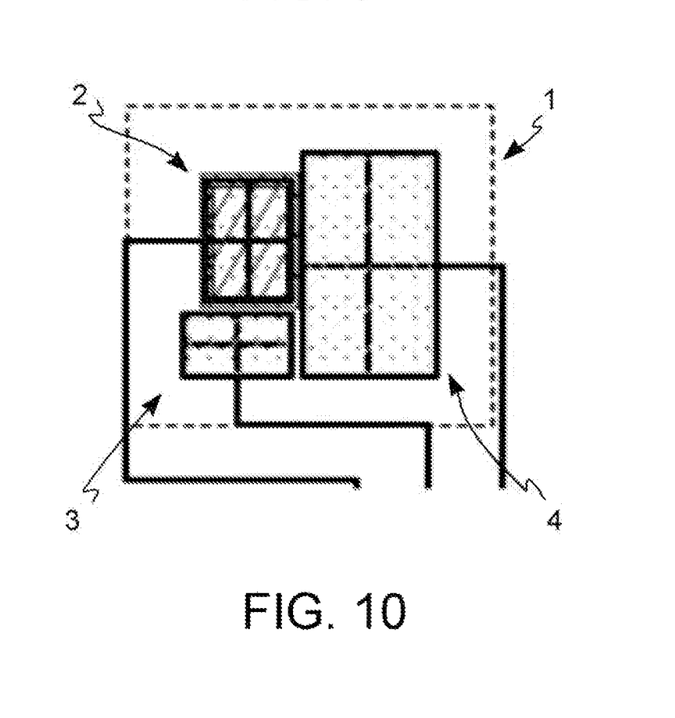

In this case, the ELISA test takes place with the use of an electrochemical probe, followed by a reading of the electrochemical type.

In a third alternative embodiment, the detection is of the capacitative type and does not require markers. In this embodiment, the device in silicon has a dielectric material on the surface on which the phage is immobilized. Following the ELISA assay, the electrical capacity of said device immersed in water is measured.

REFERENCES

Baril L, Nicolas L, Croisile B, Crozier P, Hessler C, et al. (2004) Immune response to Aβ-peptides in peripheral blood from patients with Alzheimer's disease and control subjects. Neurosci Lett 355: 226-230.

Brettschneider S, Morgenthaler N G, Teipel S J, Fischer-Schulz C, Burger K, Dodel R, Du Y, Moller H J, Bergmann A, Hampel H. (2005) Decreased serum amyloid beta (1-42) autoantibody levels in Alzheimer's disease, determined by a newly developed immuno-precipitation assay with radiolabeled amyloid β (1-42) peptide. Biol Psychiatry 57:813-816.

Britschgi M at al. (2009) Neuroprotective natural antibodies to assemblies of amyloidogenic peptides decrease with normal aging and advancing Alzheimer's disease. PNAS 106/29:12145-12150.

Bastas G et al (2008) Bioinformatic Requirements for Protein Database Searching Using Predicted Epitopes from Disease-associated Antibodies; Molecular & Cellular Proteomics 7:247-256.

Du Y, Dodel R, Hampel H, Buerger K, Lin S, Eastwood B, Bales K, Gao F, Moeller H J, Oertel W, et al. (2001) Reduced levels of amyloid beta-peptide antibody in Alzheimer disease. Neurology 57:801-805.

Gustaw K A, et al. (2008) Antigen-antibody dissociation in Alzheimer disease: A novel approach to diagnosis. J Neurochem 106:1350-1356.

Gustaw-Rothenberg K, Siedlak S, Bonda D (2010) Dissociated amyloid-beta antibody levels as a serum biomarker for the progression of Alzheimer's disease: A population-based study. Exp Gerontol 45: 47-52.

Hock C, Konietzko U, Streffer J R, Tracy J, Signorell A, Muller-Tillmanns B, Lemke U, Henke K, Moritz E, Garcia E, et al. (2003) Antibodies against beta-amyloid slow cognitive decline in Alzheimer's disease. Neuron 38:547-554.

Hughes E, Burke R M, Doig A J (2000) Inhibition of toxicity in the β-amyloid peptide fragment β-(25-35) using N-methylated derivatives. J. Biol. Chem. 275/33: 25109-25115.

Hyman B T, Smith C, Buldyrev I, Whelan C, Brown H, Tang M X, Mayeux R (2001) Autoantibodies to amyloid-beta and Alzheimer's disease. Ann Neurol 49:808-810.

Klaver A C, Coffey M P, Smith L M, Bennett D A, Finke J M, et al. (2011) ELISA measurement of specific non-antigen-bound antibodies to Aβ-42 monomer and soluble oligomers in sera from Alzheimer's disease, mild cognitively impaired, and non cognitively impaired subjects. J Neuroinflammation 8: 93.

Moir R D, Tseitlin K A, Soscia S, Hyman B T, Irizarry M C, Tanzi R E. (2005) Autoantibodies to redox-modified oligomeric Aβ are attenuated in the plasma of Alzheimer's disease patients. J Biol Chem 280:17458-17463.

Mruthinti S, Buccafusco J J, Hill W D, Waller J L, Jackson T W, et al (2004) Autoimmunity in Alzheimer's disease: increased levels of circulating IgGs binding Aβ and RAGE peptides. Neurobiol Aging 25: 1023-1032.

Nath A et al. (2003) Autoantibodies to amyloid β-peptide (M) are increased in Alzheimer's disease patients and Aβ antibodies can enhance Aβ neurotoxicity: Implications for disease pathogenesis and vaccine development. Neuromol Med 3:29-39.

Neddenriep B, Calciano A, Conti D, Sauve E, Paterson M, Bruno E, Moffet D A (2011) Short peptides as inhibitors of amyloid aggregation. Open Biotechnol J. 5:39-46.

Song M, Mook-Jung I, Lee H, Min J, Park M (2007) Serum anti-amyloid-beta antibodies and Alzheimer's disease in elderly Korean patients. J Int Med Res 35: 301-306.

Szabo P, Relkin N, Weksler M E (2008) Natural human antibodies to amyloid β peptide. Autoimmun Rev 7:415-420.

Weksler M E, Relkin N, Turkenich R, Larusse S, Ling Z, et al. (2002) Patients with Alzheimer disease have lower levels of serum anti-Amyloid peptide antibodies than healthy elderly individuals. Exp Gerontol 37: 943-948.

The invention claimed is:

1. A peptide comprising the amino acid sequence selected from the group comprising: NH2-RWPPHFEWHFDD-COOH (SEQ ID NO: 1), NH2-GGGCIEGPCLEG-COOH (SEQ ID NO: 4), and NH2-HRGCIEGPCLDA-COOH (SEQ ID NO: 5).

2. A method for diagnosing Alzheimer's disease (AD) in a subject comprising preparing a phage clone expressing a peptide comprising the amino acid sequence NH2-RWPPHFEWHFDD-COOH (SEQ ID NO: 1); exposing precipitate of said phage clone to a subject's serum; after suitable incubation and washings, incubating with an anti-human IgG antibody; detecting the results of reaction, wherein a positive result of the reaction is indicative of AD pathology.

3. A method for detecting an antibody in a sample comprising preparing a phage clone expressing a peptide of claim 1; exposing precipitate of said phage clone to the sample; after suitable incubation and washings, incubating with an anti-human IgG antibody; detecting the results of reaction, wherein a positive result of the reaction is indicative of antibodies in the sample that bind the peptide of claim 1.

* * * * *

SEQUENCE LISTING

```
<160> NUMBER OF SEQ ID NOS: 12

<210> SEQ ID NO 1
<211> LENGTH: 12
<212> TYPE: PRT
<213> ORGANISM: Homo sapiens

<400> SEQUENCE: 1

Arg Trp Pro Pro His Phe Glu Trp His Phe Asp Asp
1               5                   10

<210> SEQ ID NO 2
<211> LENGTH: 23
<212> TYPE: DNA
<213> ORGANISM: Homo sapiens

<400> SEQUENCE: 2
gctaccctcg ttccgatgct gtc                                              23

<210> SEQ ID NO 3
<211> LENGTH: 17
<212> TYPE: DNA
<213> ORGANISM: Homo sapiens

<400> SEQUENCE: 3
gttttcccag tcacgac                                                     17
```

```
<210> SEQ ID NO 4
<211> LENGTH: 12
<212> TYPE: PRT
<213> ORGANISM: Homo sapiens

<400> SEQUENCE: 4

Gly Gly Gly Cys Ile Glu Gly Pro Cys Leu Glu Gly
1               5                   10

<210> SEQ ID NO 5
<211> LENGTH: 12
<212> TYPE: PRT
<213> ORGANISM: Homo sapiens

<400> SEQUENCE: 5

His Arg Gly Cys Ile Glu Gly Pro Cys Leu Asp Ala
1               5                   10

<210> SEQ ID NO 6
<211> LENGTH: 42
<212> TYPE: PRT
<213> ORGANISM: Homo sapiens

<400> SEQUENCE: 6

Asp Ala Glu Phe Pro His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 7
<211> LENGTH: 10
<212> TYPE: PRT
<213> ORGANISM: Homo sapiens

<400> SEQUENCE: 7

Ala Ala Asn Ser Ala Gln Pro Asp Ile Lys
1               5                   10

<210> SEQ ID NO 8
<211> LENGTH: 22
<212> TYPE: PRT
<213> ORGANISM: Homo sapiens

<400> SEQUENCE: 8

Lys Gln Lys Phe Asn Pro Asp Lys Asp Val Gly Val Phe Val Gln Phe
1               5                   10                  15

Ala Ile Asn Asn Cys Ile
            20

<210> SEQ ID NO 9
<211> LENGTH: 42
<212> TYPE: PRT
<213> ORGANISM: Homo sapiens

<400> SEQUENCE: 9

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

```
<210> SEQ ID NO 10
<211> LENGTH: 34
<212> TYPE: PRT
<213> ORGANISM: Homo sapiens

<400> SEQUENCE: 10

Ala Glu Gly Glu Phe Arg Trp Pro Pro His Phe Glu Trp His Phe Asp
1               5                   10                  15

Asp Gly Asp Pro Ala Lys Ala Ala Phe Asp Ser Leu Gln Ala Ser Ala
            20                  25                  30

Thr Glu

<210> SEQ ID NO 11
<211> LENGTH: 34
<212> TYPE: PRT
<213> ORGANISM: Homo sapiens

<400> SEQUENCE: 11

Ala Glu Gly Glu Phe Gly Gly Gly Cys Ile Glu Gly Pro Cys Leu Glu
1               5                   10                  15

Gly Pro Asp Pro Ala Lys Ala Ala Phe Asp Ser Leu Gln Ala Ser Ala
            20                  25                  30

Thr Glu

<210> SEQ ID NO 12
<211> LENGTH: 34
<212> TYPE: PRT
<213> ORGANISM: Homo sapiens

<400> SEQUENCE: 12

Ala Glu Gly Glu Phe His Arg Gly Cys Ile Glu Gly Pro Cys Leu Asp
1               5                   10                  15

Ala Pro Asp Pro Ala Lys Ala Ala Phe Asp Ser Leu Gln Ala Ser Ala
            20                  25                  30

Thr Glu
```